United States Patent [19]

Schleuniger et al.

[11] Patent Number: 4,691,576
[45] Date of Patent: Sep. 8, 1987

[54] METHOD OF TESTING THE MECHANICAL STRESS RESISTANCE OF A SAMPLE OF MATERIAL AND APPARATUS FOR CARRYING OUT THE METHOD

[75] Inventors: Kurt Schleuniger, Nennigkofen; Peter Hermann, Brügg bei Biel, both of Switzerland

[73] Assignee: Strausak AG, Switzerland

[21] Appl. No.: 801,685

[22] PCT Filed: Mar. 1, 1985

[86] PCT No.: PCT/CH85/00036
 § 371 Date: Jan. 21, 1986
 § 102(e) Date: Jan. 21, 1986

[87] PCT Pub. No.: WO85/04247
 PCT Pub. Date: Sep. 26, 1985

[30] Foreign Application Priority Data

Mar. 21, 1984 [CH] Switzerland .................. 1416/84

[51] Int. Cl.$^4$ .............................................. G01N 3/00
[52] U.S. Cl. .............................................. 73/821
[58] Field of Search ............... 73/836, 806, 789, 825, 73/821, 818, 807, 837, 816

[56] References Cited

U.S. PATENT DOCUMENTS

| | | |
|---|---|---|
| 3,610,034 | 10/1971 | Gunn et al. |
| 3,858,442 | 1/1975 | Nozaki |
| 4,022,056 | 5/1977 | Barland ........................... 73/78 |
| 4,448,079 | 5/1984 | Schumacher et al. ........... 73/789 |

FOREIGN PATENT DOCUMENTS

| | | |
|---|---|---|
| 2089214 | 1/1972 | France |
| 2111397 | 6/1972 | France |

Primary Examiner—Jerry W. Myracle
Attorney, Agent, or Firm—Ostrolenk, Faber, Gerb & Soffen

[57] ABSTRACT

To measure the stress resistance of a material sample, the motions of two jaws which hold the material sample are kinematically coupled via the sample. The jaw which is on the side toward which the motion takes place is subjected to a local variable force (F) which is transmitted to the sample as stress. The sample breaking moment is detected and knowing the relationship between the motion of the jaw which is subjected to the force and said force, it is possible to calculate the stress to which the sample is subjected. By taking into account the detected translation required for the test and by optionally proceeding to time measurements with a given translation speed, it is possible to adjust the motion of the jaws.

28 Claims, 11 Drawing Figures

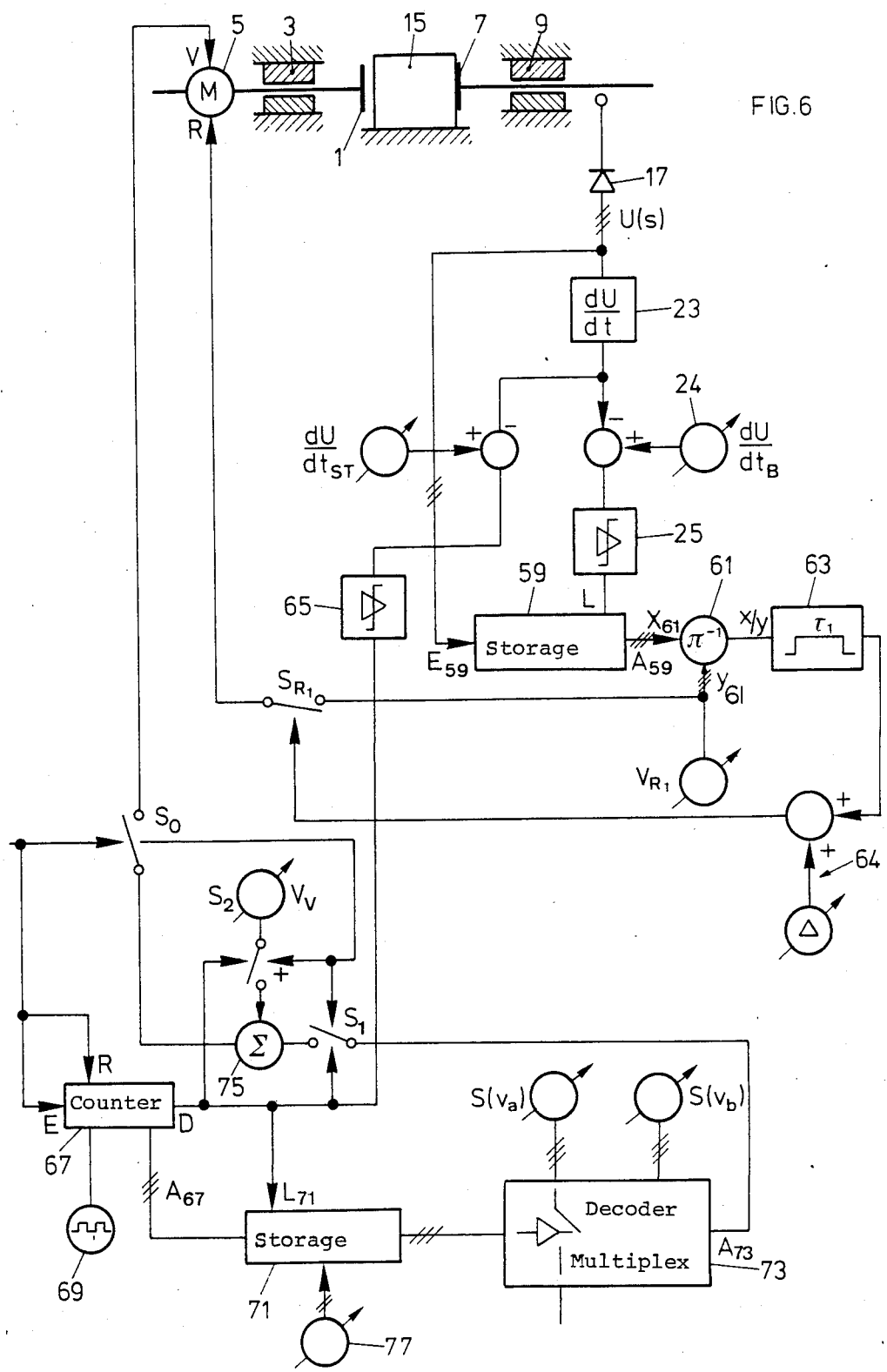

METHOD OF TESTING THE MECHANICAL STRESS RESISTANCE OF A SAMPLE OF MATERIAL AND APPARATUS FOR CARRYING OUT THE METHOD

BACKGROUND OF THE INVENTION

The present invention relates to a method of testing the mechanical stress resistance of a sample of material in which the movement of two jaws is coupled via the sample and one jaw, as the loading jaw, acts back on the sample with a force which varies with the position of the jaw. It relates furthermore to an apparatus for carrying out this method, the loading jaw being coupled with a force-producing member. It also relates to the use of the method.

Such methods are used, as is known, for testing samples of material, for instance, the compressive strength of tablets, but also, of other samples such as electronic components. Thus it is known, for instance, from Swiss Pat. No. 523 499 of the same applicant, to place such samples of material, and particularly tablets, between two jaws, one of which is driven forward until it contacts the tablet. The two jaws are then coupled in movement via the tablet. The second jaw is also now pushed along, thereby pushing a gravity pendulum out of its vertical position of rest. The pendulum thus acts on the tablet with a force which varies with the position of the jaw. By means of a suitably graduated maximum deflection indicator it is recorded when and upon what deflection of the pendulum the sample of material, and in this case in particular the tablet, breaks.

Other methods are also known in which the position-dependent force is produced by spring arrangements. Each of these methods has the disadvantage that to obtain an unequivocal association between the position of the jaw acted on by the force and the force thereby exerted on the specimen is expensive and/or inaccurate. Furthermore, the problem arises in the known methods that they do not operate with optimal time control in the sense that the movements of the jaws, whether in the forward cycle, and in particular until contact is made with the sample of material, i.e. up to the coupling in motion of the two jaws via the sample of material, and/or in the jaw return cycle, are not so controlled that the measurements are effected as rapidly as possible but without inaccuracies, which, however, time optimalizing in the forward cycle as well as in the return cycle would produce. In this connection, however, it must be borne in mind that the forwardly driven jaw must make such soft contact with the sample of material that the contact momentum will not by itself, particularly in the case of samples of brittle material, lead to breakage phenomena which might not be visible but which would falsify the result.

SUMMARY OF THE INVENTION

An important purpose of the present invention is to improve the aforementioned method and the corresponding apparatus in such a manner that the above-mentioned disadvantages are eliminated, i.e. an accurate measurement of the breaking load is possible, and that this be done with relatively little expense and with time-optimal control of the movement of the jaws.

This result is achieved in the manner that the path of displacement of at least one of the jaws is determined and that from a knowledge of the dependence of the force of the loading jaw on its position, at least directly before the breaking of the sample, the force then acting back on the sample is calculated and/or, from the determination of the path of displacement and possibly a knowledge of the conditions as to speed of the one jaw or other, their movement is controlled.

By determination of the path of displacement of the loading jaw and calculation of the force acting back on the sample from the knowledge of the position-force dependence, at least directly before the breaking of the sample, an exact, reproducible determination of the breaking load is possible.

If the displacement path is determined directly or indirectly via a time measurement when the speed conditions of the two jaws are known, there is then the possibility of carrying out distance/force tests such as stress/strain tests, or distance/force/time tests such as alternate loading tests.

Due to the fact that from the direct or indirect determination of the displacement path and possibly a knowledge of the speed conditions of one and/or the other jaw their movement is controlled, a time-optimal control of the movement of the jaws in principle both in the return and in the forward cycle is furthermore possible, either as alternative or in addition at relatively slight expense and this since only a determination of the path on the one jaw is necessary for this.

The time of breakage is in this connection preferably detected by detection of a pre-established discontinuity with respect to time of the displacement path determined, which in its turn results in a simplification of the system since the direct determination of the displacement path which must then in any event be effected can also be used for the detection of the time of breakage.

The return movement of the other jaw, i.e. of the forward driven jaw, is optimized by the fact that, from the determination of the displacement path of the loading jaw up to directly before the breaking of the sample and pre-establishing of the return speed of the other, i.e. forward driven jaw via determination of its return time its return is controlled.

In other words, as from the time when the two jaws are coupled in motion via the sample, the path of displacement of the entire system is measured directly or via a time measurement, corresponding to the path of the loading jaw, up to directly before the breaking of the sample or the commencement of the breaking of the sample, and from this path value and pre-establishment of the speed of return of the drive jaw there is determined the time during which, with the said return speed, the latter must be returned.

In this connection the return time of the other jaw, the driven jaw, is preferably calculated and a time tolerance time interval, such as is in accord with the geometric balance of the sample expansion and breakage path is added thereto, said other jaw being returned with pre-established speed during the total time interval, for instance in the manner that a pre-established jaw spacing is again established for the insertion of the next sample. For the optimizing of the forward movement, one preferably proceeds in the manner that a speed/advance-path or advance-time profile of the other jaw is pre-established for its advance in the case of one sample and the profile is adaptively optimized for the next sample on basis of a jaw/sample-contacting criterion in the case of said first sample.

In this connection, one preferably proceeds in the manner that a speed/displacement-path or displacement-time profile of the other jaw is pre-established for its advance in the case of one sample, its time of commencement of displacement is recorded, a point of time at or after the start of the displacement of the loading jaw is recorded and the profile for the next sample is adaptively corrected with due consideration of sample tolerances based on a knowledge of the range of difference of the point of time and of the profile in the case of the one sample, for the optimalizing in time of the advance of the other jaw and the maintaining of a pre-established contact momentum between the jaws and the corresponding sample.

An apparatus such as one for the carrying out of the method in which the loading jaw is coupled with a member which produces a force which is dependent on position has, at least for one of the jaws, a path measuring device for the direct measurement of the path or for the measurement of the displacement time and, via speed, for the indirect measurement of the path.

In order to produce a precise indication for the sample breaking load, the output of the path measuring device is fed as input to an evaluation unit which acts as function generator, the evaluation unit giving off, as a function of the output signal of the path measurement device, a signal which is proportional to the force acting on the loading jaw. In order to create a highly stable force-producing member which is as free as possible of fatigue, the member is preferably developed as a gravitational pendulum which is swung out of the vertical by displacement of the loading jaw. The path measuring device is then developed in simple manner as angle recorder on the pendulum.

In order to take into account the dependence on the angle of swing of the force acting on the sample, the evaluation unit is now provided with a sine-function unit whose input is connected with the output of the angle recorder.

In order to take into account the fact that the measurement device may possibly not be set up in such a manner that the pendulum vertical agrees with the zero reading of the angle recorder it is proposed that the evaluation unit comprise a superimposing unit which is arranged in front of the sine function unit and at which there is added to the output signal of the angle recorder a signal which corresponds to an offset angle in order to take into account the relative angular position between jaw movement path and the vertical.

For the calibration of the apparatus it is proposed that the evaluation unit comprise a storage element for the offset angle signal, this signal preferably being taken from the output of the angle recorder in the position of rest of the apparatus. In this way it is made possible that the instrument be set up and that the deviation between vertical position of the pendulum and zero position of the angle recorder which exists to be stored as offset position difference in the storage so as to be subsequently taken into account upon the calculation of the breaking load. If the loading jaw is coupled in motion with the pendulum by means of a deflection mechanism, as will ordinarily be the case, the evaluation unit will be provided with a linearization function unit to which the output signal of the angle recorder is fed and whose output signal as factor dependent on angle of swing is connected to the output signal of the sine function unit on a weighting unit. In this way, the geometrical transmission ratios dependent on the angle of swing of the pendulum between the jaw and the pendulum can be taken into account, which leads to an accurate calculation of the breaking load.

If the output of the path measurement device is brought to a storage device for the storing of a signal of the path measurement device corresponding to the path traversed by the force-impacted loading jaw until the breaking of the sample or the period of time used for this, with a given course of the speed and with the output of the storage unit via a weighting unit to which there can be fed as weighting factor a signal corresponding to the return speed of the other jaw, namely the driven jaw, and is brought to a time or path control unit via a drive for the other jaw and the return thereof is controlled, then the result is obtained that with the path measuring device provided the return movement of the other driven jaw can be optimally controlled also only on the loading jaw.

In this connection, a variable adjustment device such as a time adjustment device is advantageously provided in order externally to lengthen the return path, whereby the driven jaw is returned with pre-established return speed not only during the time which corresponds to the displacement path of the loading jaw but longer, in such a manner that, on the one hand, sample tolerances can be taken into account and, on the other hand, assurance can be had that in the condition of rest of the apparatus sufficient space is maintained between the jaws for the insertion of the sample. Therefore, the displacement path of the loading jaw up to the breaking of the sample is measured in the manner that by dividing this portion of the path by the return speed of the driven jaw there is determined the portion of time during which the latter is at least to be returned at this speed or, instead of the portion of path, the time necessary for this is measured and with a knowledge of the advance and return speed ratios the said portion of time is determined.

If a time measuring device is provided which records the portion of time between start of displacement of the other jaw, i.e. of the driven jaw, and that at or after the loading jaw upon the testing of the sample and retains it, and if the output of this time measuring device acts on a speed/advance-path or speed/advance-time profile control unit for a drive for the other jaw, the driven jaw, in connection with which the time measuring device with the portion of time determined for a sample testing controls the advance speed-time profile of the other jaw, the driven jaw, upon the next sample testing, then the result is obtained that by adaptation from the measurement of how long it takes, until the driven jaw from the start of the displacement contacts the sample in the case of the one sample the profile is determined upon the advance of the jaw for the next sample and the drive is then controlled accordingly. In this way a time-optimal advance and the maintaining of a maximally tolerated momentum impulse between driven jaw and sample are assured.

As already mentioned, in the case, for example, of the method proposed and, for example, of the apparatus proposed, the one jaw is driven and acts via the sample on the loading jaw. If the breaking of the sample now takes place then, if suitable measures are not taken, the loading jaw will suddenly bounce back against the drive jaw, at least as far as the broken pieces of sample between them permit or else, if the driven jaw has already been moved back, which is possible with high speed, the loading jaw will rapidly move unbraked back into its starting position. This, depending on the masses present, leads to large mechanical momentums with corresponding mechanical stresses.

In order to prevent this, it is now proposed that the breaking of the sample be detected and the loading jaw returned into its position of rest with controlled or regulated acceleration. If the acceleration is controlled as a function of the path of displacement of the loading jaw then, furthermore, the path of displacement of the loading jaw will preferably already be detected prior to the breaking of the sample and the breaking will be detected by the occurrence of a pre-established discontinuity in time in the jaw displacement path.

The apparatus is so developed for this purpose that a return-accelerating control device is provided for the loading jaw, or a return control with the device as setting member, in which connection the control device is preferably a braking device which exerts a braking force which is a function of the position of the jaw or produces a braking force of pre-established time dependence.

If the braking force is to be controlled, it is proposed that the output of a path measuring device act at least momentarily on a control input of an accelerating control device for the loading jaw.

In this connection the force-producing member is preferably a gravitational pendulum which is swung from the vertical by displacement of the loading jaw and the accelerating control device is a brake which acts on the pendulum.

The brake preferably comprises a friction plate which acts on the pendulum in a plane parallel to the plane of swing of the pendulum the plate being displaceable at least in one component perpendicular to said plane and being connected, upon controlled braking, with a controllable drive, such as an electromagnetic linear drive, or with a time control unit for controlling a pre-established time function of the braking force.

The path measuring device is in this connection preferably developed as an angle recorder on the pendulum and is connected with a differentiation unit whose output is fed to a comparator circuit, preferably with adjustable reference value, the output of the comparator circuit blocking the brake or releasing it for controlled placing in operation.

By means of the differentiation unit with comparator circuit behind it, if the breaking of the sample and the time discontinuity which thus takes place is detected in the path recording, then the brake is switched from the blocked condition to the controlled activated condition.

In the manner that for pressure/path or pressure/path/time testing of materials, one measures, directly or indirectly, the displacement path of both jaws or associates a path measuring device with each of the two jaws for this purpose, a large number of dynamic tests are possible, such as stress/strain tests or alternating stress tests.

BRIEF DESCRIPTION OF THE DRAWINGS

The invention will now be explained, by way of example, with reference to the figures in the drawing, in which:

FIG. 6 is a functional block diagram of a device according to the invention with the function blocks for controlling the jaw advance and return movements.

DETAILED DESCRIPTION OF PREFERRED EMBODIMENTS

Figure 1:
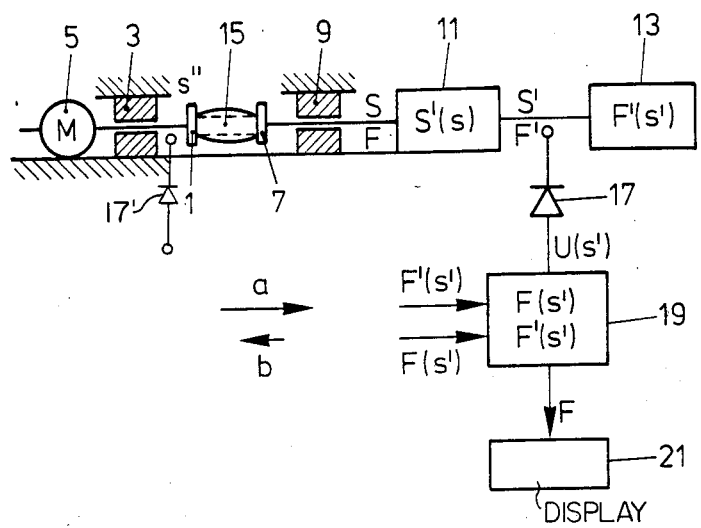
FIG. 1 shows diagrammatically the construction of an apparatus according to the invention for the pressure-load testing of samples of material.

FIG. 1 diagrammatically shows an apparatus in accordance with the invention. It comprises a driven jaw 1 which is supported displaceably in longitudinal guides 3 and is connected to a drive motor 5. There is also provided a mating jaw 7, also mounted for longitudinal displacement in guides 9, which acts on a force-producing unit 13 via a deflection mechanism 11 such as a transmission or a system of rods. The path of displacement of the jaw 7, referred to hereinbelow as the force-impacted jaw because of the force acting on it, is designated s, while the force acting on the force-impacted jaw 7 in the direction opposite the direction of displacement is designated F. The deflection mechanism 11 transforms the path S passed over by the force-impacted jaw 7 in accordance with a pre-established function into the path s'(s) on the output side and acts with this displacement on the force-producing member 13, for instance a spring member, or, as will be described further below, preferably a gravitational pendulum which is deflected out of the vertical. The force-producing member 13 acts with the force F'(s') as a function of the initial displacement s' of the transmission mechanism 11 from the output side back onto the transmission mechanism 11, and the transmission mechanism 11 transmits this force according to a given transmission function as force F back to the force-impacted jaw 7. A sample of material 15 which is to be tested is placed between the jaws 1 and 7.

In accordance with the invention, the displacement path produced in the force-impacted jaw, whether it be s or s' as shown in FIG. 1, is now in general detected by a path detector 17, preferably a mechanical/electrical transducer such as a potentiometer, and an electric signal U(s') which is proportional to the displacement path detected, in this case s', appears at the output of the path detector 17. This signal is fed to a function generator 19 in which the dependence of the force F' of the force-producing member 13 on its input-side displacement path s' is stored, in the same way as the dependency function of the force F acting on the jaw 7 and thus acting back on the sample 15 as a function of the displacement s' is stored on the output side of the transmission mechanism 11. With the signal U(s') which corresponds to the path of displacement moved over at the time by the force-impacted jaw 7 as input variable, the function generator 19 determines, on the basis of the said stored functions, the instantaneous loading force F on the sample and outputs F on the output side in general to a display 21 or a recorder. The displacement path s' can in this connection also be determined indirectly by a time measurement, with the speed of advance known.

It is now essential for the force F acting on the sample 15 to be displayed when the sample 15 breaks. This is achieved, in accordance with FIG. 2, by feeding back the output signal U(s') of the path detector 17 to a differentiation unit 23. In view of the fact that at the time of the breaking of the sample the force-impacted jaw 7, which previously moved in the direction indicated by $\underline{a}$ in FIG. 1, moves back rapidly, in proportion to the reduction of the size of the sample, driven forcefully in the direction $\underline{b}$ against the drive jaw 1, the time of breakage is determined from the monitoring of the time derivative of the output signal of the path detector 17 in the manner that said time derivative dU/dt is compared by a comparator circuit 25 with a predetermined or predeterminable time derivative $dU/dt_B$, supplied by a unit 24, which is recognized as significant for the breaking of the sample. If the time derivative of the output signal of the path detector 17 which is determined exceeds the pre-established value, then the comparator 25, for instance by means of an output pulse, activates a storage circuit 27, for instance an S & H circuit, whereby the output signal value of the path detector 17 which is then momentarily present is taken over and fed as break-specific, path-proportional $U(s'_B)$ to the function generator 19.

As already explained with reference to FIG. 1, the function generator 19 determines from this the sample load F which is then prevailing and forwards it to the display 21 or a recorder. Further evaluations such as establishing of statistics, etc., are possible with these values. Furthermore, if strains of the samples upon the stressing are of interest or if alternating stressing tests are to be carried out, then a second displacement path s'' of the jaw 1 can also be measured with a second path detector 17'. This path detection can also be effected indirectly by time measurement, if the advance-speed conditions are known.

Figure 3:
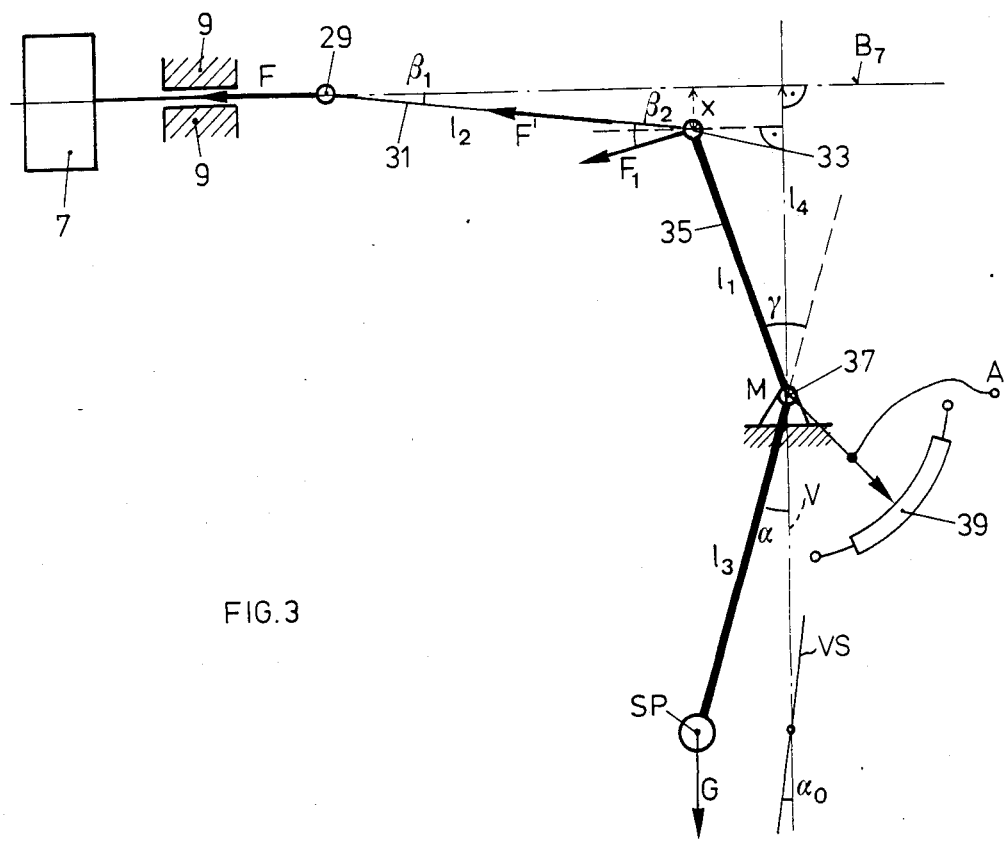
FIG. 3 shows diagrammatically a jaw coupled with a gravitation pendulum and the geometrical variables to be taken into consideration in this connection, on a preferred variant of the embodiment of the apparatus shown in FIG. 1.

FIG. 3 shows, by way of example, an embodiment of the transmission mechanism 11 and of the force-generating member 13 and the variables which lead to the determination of the functions defined in FIG. 1 or analogous functions. The force-impacted jaw 7, which is guided horizontally in the bearings 9, acts via a joint 29 on a transmission lever 31 of the length $l_2$, which lever is connected at an articulation 33 to a pendulum 35. The weight G of the pendulum 35 is shown as acting at the center of gravity SP of the pendulum and the pendulum is swingably mounted on a bearing 37. The distance between the center of gravity SP of the pendulum and the pendulum bearing 37 is designated $l_3$ and the distance between the pendulum bearing 37 and the articulation 35 is designated $l_1$. The pendulum 33 acts as the member referred to as the force-producing member 13 in FIG. 1 and the connecting lever 31 acts as transmission mechanism 11. If we designate by $\alpha$ the deviation of the pendulum arm $l_3$ from the vertical V and by $\alpha_o$ the deviation of the vertical of the apparatus VS with respect to the vertical V there is then obtained the moment of rotation exerted by the weight G of the pendulum with respect to its bearing 37, namely:

$$M = G \cdot l_3 \cdot \sin(\alpha - \alpha_o) \quad (1)$$

There thus results a force $F_1$ perpendicular to the pendulum arm $l_1$, as shown in the drawing, equal to:

$$F_1 = M/l_1 \quad (2)$$

If $l_4$ is the distance of the pendulum articulation 37 from the path of movement $B_7$ of the jaw 7 and $\gamma$ is the rigid angular position of the pendulum arm $l_1$ with reference to the pendulum arm $l_3$, then the distance x of the articulation 33 from the jaw path $B_7$ as a function of the swing of the pendulum is:

$$x = l_4 - l_1 \cdot \cos(\gamma - \alpha) \quad (3)$$

In this way, the angle $\beta_1$ between the transmission lever 31 and the path of movement $B_7$ is:

$$\beta_1 = \arcsin(x/l_2) \quad (4)$$

and the angle $\beta_2$ between the force $F_1$ and the transmission lever 31 is:

$$\beta_2 = \beta_1 + \gamma - \alpha. \quad (5)$$

From this we obtain for $\beta_1$:

$$\beta_1 = \arcsin \frac{l_4 - l_1 \cdot \cos(\gamma - \alpha)}{l_2} \quad (6)$$

The force F' acting in the direction of the transmission lever 31 and therefore, in the case of FIG. 1, the force which acts between the force-producing member 13, in this case the pendulum 35, and the transmission mechanism 11, in this case the transmission lever 13, is:

$$F' = F_1 c/\cos \beta_2 \quad (7)$$

From this there results for the force F which in accordance with FIG. 1 acts from the transmission mechanism 11, here the transmission lever 31, on the jaw 7:

$$F = F_2/\cos \beta_1 \quad (8)$$

and, taking equation (6) into consideration, the dependence:

$$F = G \frac{l_3}{l_1} \frac{\cos \beta_1}{\cos(\beta_1 + \gamma - \alpha)} \cdot \sin(\alpha - \alpha_o) \quad (9)$$

on the angle of swing $\alpha$ of the pendulum, similar to the path variable S' of FIG. 1.

As diagrammatically shown in FIG. 3, the angle of swing $\alpha$, with due consideration of the deviation in position $\alpha_o$ is determined with an angle recorder, for instance a potentiometer 39, whose center tap swings together with the pendulum around the pendulum support 37.

Figure 4:
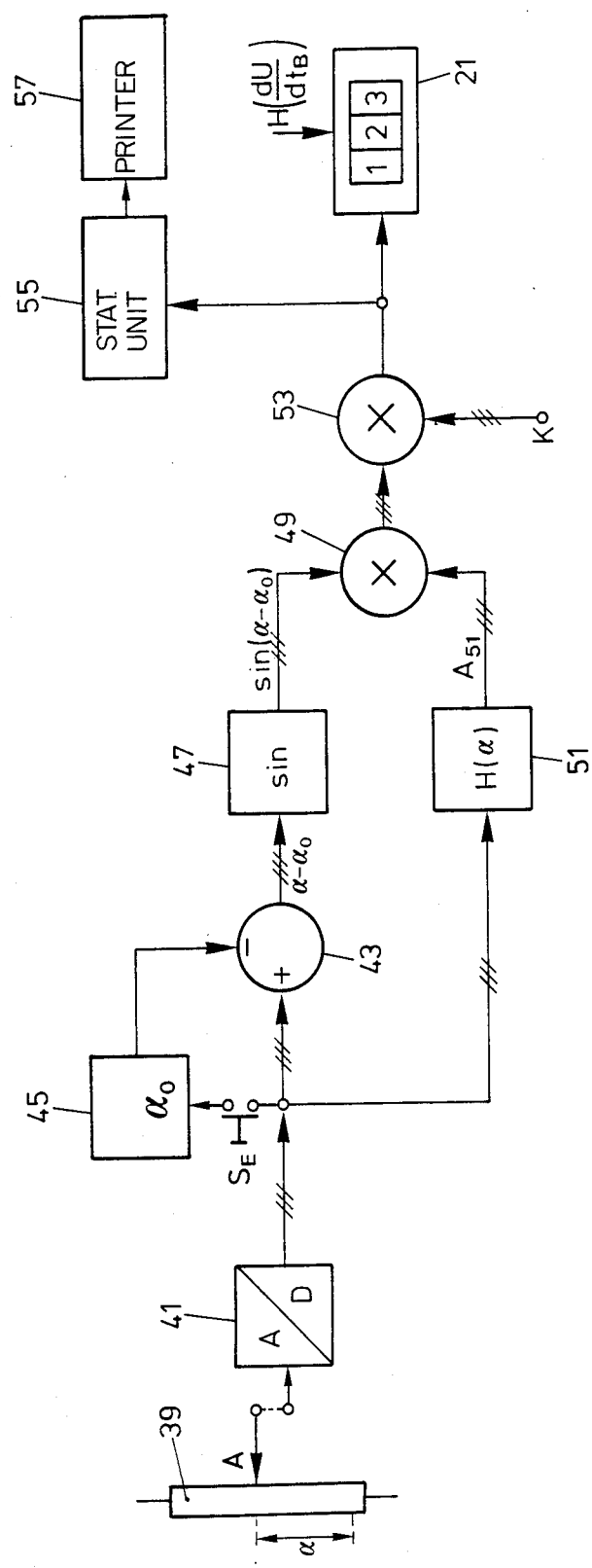
FIG. 4 is a functional block diagram of an evaluation device on an apparatus with gravitational pendulum according to FIG. 3.

In FIG. 4 is shown the construction of the function generator 19 of FIG. 1 for determining the functions described above in connection with FIG. 3. From the potentiometer 39, an electric signal corresponding to the angle of swing α is tapped off in accordance with FIG. 3 from the tap A and fed to an analog/digital converter 41. The digital output of the converter 41 is fed to the one input of an addition unit 43. Via a calibration switch $S_E$, the output of the converter 41 can be connected briefly to a storage 45, which receives the value then present at the output of the converter 41, and, when the apparatus is at rest, thus corresponding to the angle value $α_o$ of FIG. 3.

The output of the storage 45 is subtracted at the addition unit 43 from the output signal of the analog/digital converter 41 so that a signal corresponding to the angle size $α - α_o$ appears at its output. This signal is fed to a sine function unit 47 which produces, at its output, a signal corresponding to the function $\sin(α - α_o)$. This signal is fed to the one input of a weighting unit 49, such as a digital multiplication unit. The output signal of the analog/digital converter 41 is fed further to a linearization function unit 51 which, in accordance with equation (9), determines the linearization function H(α) corresponding to $$H(α) = \frac{\cos β_1}{\cos(β_1 + γ - α)} \tag{10}$$

in which $$β_1 = \arc \sin\left(\frac{l_4 - l_1\cos(γ - α)}{l_2}\right) \tag{11}$$

Figure 5:
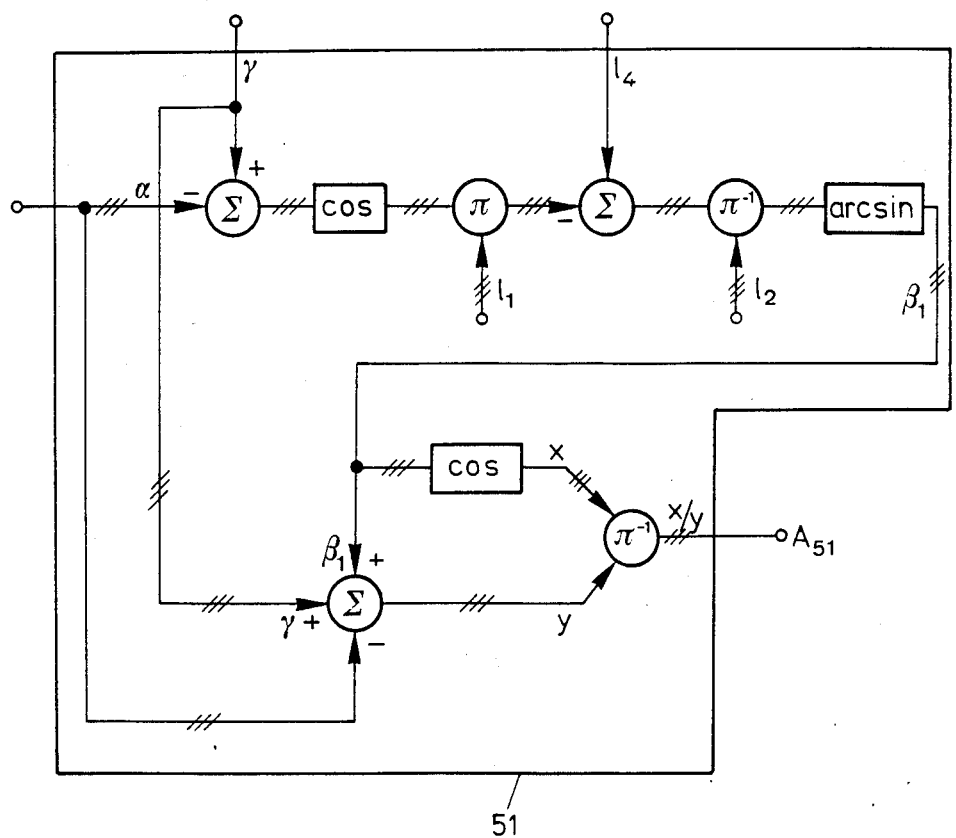
FIG. 5 is a functional block diagram of a linearization unit in the evaluation unit according to FIG. 4.

The construction of the linearization function unit 51, i.e. the realization of this function from a circuit or function block standpoint, is shown in FIG. 5, which requires no further explanation in view of equations (10) and (11). It is also self-evident that all signal paths are digital multi-line paths, as indicated by the lines bearing the three slashes. The output $A_{51}$ of the linearization function unit 51 is fed to the second input of the weighting unit 49 and is combined multiplicatively with the output of the sine function unit 47. The output of the weighting unit 49 is fed via another weighting unit 53 in which it is coupled with the pendulum constant K, in particular its weight variable. The output of the weighing unit 49 is provided to the display 21 and is also conducted to a subsequent printer 57, possibly via a statistical unit 55. The determining of the breaking load value is, as has been explained with reference to FIG. 2, effected for instance by detection of the breakage discontinuity in the course of the angle variable α in the manner that, upon the occurrence of the criterion which has been explained with reference to FIG. 2, the system initiates the desired output display by generating, for example, a hold signal $H(dU/dt_B)$.

With reference to FIG. 6, it will now be explained how, by means of the path detection, as explained on basis of the previous figures, the movements of the jaws are controlled. The output of the path detector 17 is fed to the input $E_{59}$ of a storage element 59. The output of detector 17 is also fed to the differentiation unit 23, which has already been described with reference to FIG. 2, and then to the comparator 25 where the instantaneous time derivative of the output signal of the detector 17 is compared with a predetermined break-specific derivative or discontinuity $dU/dt_B$, which is provided by an input unit 24. The load time of the storage 59 is established by the appearance of a load signal L; in other words, the storage 59 receives a signal which corresponds to the displacement path of the power-impacted jaw 7 up to the time of breakage. The output $A_{59}$ of the storage 59 is fed to an input $X_{61}$ of a weighting unit 61 to which at a second input $Y_{61}$ an adjustable signal corresponding to the return speed $V_{R1}$ of the driven jaw 1 is fed. The weighting unit 61, developed as a ratio former, gives off an output signal which corresponds to the quotient of breakage displacement path at the output $A_{59}$ of the storage 59 divided by recovery speed $V_{R1}$ of the jaw 1. It is therefore self-evident that the time interval can also be directly measured and correspondingly stored and, in case of known advance-speed conditions, corresponds to the path of displacement of the jaw 7 up to the time of breakage. In general, all path measurement devices described can be or comprise time measurement devices, provided the speeds of advance are known.

The above-mentioned output signal is fed to a time control unit 63 which gives off an output pulse having a pulse duration $τ_1$ (x/y) which corresponds to the output signal of the weighting unit 61, i.e. corresponds to the period of time which the jaw 1 requires in order to pass over the breakage path with a given return speed $V_{R1}$. The output pulse of the time control unit 63 is extended externally by a predeterminable time variable $Δ$ and acts via a control circuit $S_{R1}$ in activating fashion on a return control input R of the motor 5 as long as this is determined by the output pulse of the time control unit 63, lengthened by the period of time $Δ$ which can be introduced. During this time, a control signal corresponding to the introduced return speed $V_{R1}$ is present on the return control input R of the motor 5; in other words, during this time the jaw 1 is returned with predetermined speed $V_{R1}$ thus by an amount equal to the breakage displacement path and an additional displacement path entered with the time variable $Δ$. The additional displacement path corresponding to the pulse lengthening $Δ$ introduced is determined on the basis of the tolerances of the sample 15 and takes into account a handling distance which must be maintained for the insertion of the next sample between the jaws 1 and 7.

In this way, the return movement of the driven jaw 1 is controlled from the determination of the displacement path of the jaw 7.

In order now to control the approach feed of the driven jaw 1 from the start of the displacement until the contacting of the sample 15 so as to effect this operating cycle optimally from the standpoint of time and to prevent too large an impingement momentum of the jaw 1 on the sample 15, the commencement of the displacement of the $dU/dt_{ST}$ force-impacted jaw 7 is determined via the differentiation unit 23 in the manner that, once again, the instantaneous time derivative of the displacement path is compared by a comparator circuit 65 with a predetermined derivative. Here the predetermined time derivative $dU/dt_{ST}$ is the zero value, since it must be detected when the jaw 7 accelerates from standstill.

The advance of the driven jaw 1 is produced by a starting switch $S_o$ in the manner that an advance control input V for the motor 5 is actuated. At the same time, upon the closing of the control switch S', a counter 67 is reset and freed for counting and it then counts the pulses of a clock oscillator 69. As soon as the output signal of the comparator 65 shows that the jaw 7 is in movement and thus the jaw 1 has contacted the sample 15, the counter 67 is stopped and at the same time the counter output $A_{67}$ is loaded into a storage 71 by activation of a load input $L_{71}$. The value now loaded in the storage 71 corresponds to the period of time which the jaw 1 needed from the start of the displacement until the contacting of the sample. A decoder multiplex circuit 73 is controlled with this value, on the output side of the storage 71. The decoder multiplex circuit 73 switches a plurality of adjustable signals $S(v_a)$, $S(v_b)$ etc., which correspond to the speed of advance, on its output $A_{73}$ in a time succession controlled by the output signal of the storage 71 or corresponding to the instantaneous position of the jaw. The output of the decoder multiplex circuit 73 is fed via a switch $S_1$ to an addition unit 75 whose output acts via the switch $S_0$ on the advance control input V of the motor 5. The addition unit 75 is also fed an adjustable signal $V_v$ via a switch $S_2$, this signal $V_v$ corresponding to the speed of advance of the jaw 1 after contacting the sample 15, i.e. it controls the actual stressing of the sample 15. While after actuation of the advance release switch $S_0$ the switch $S_1$ is closed and the switch $S_2$ is opened, upon detection of the commencement of the displacement of the jaw 7 the switch $S_1$ is opened and the switch $S_2$ closed. Thus the speed of advance of the jaw 1 prior to the contacting of the sample 15 is controlled by the output of the decoder multiplex circuit 73 and thereafter by the pre-established speed of advance corresponding to the signal $V_v$.

Figure 6A:
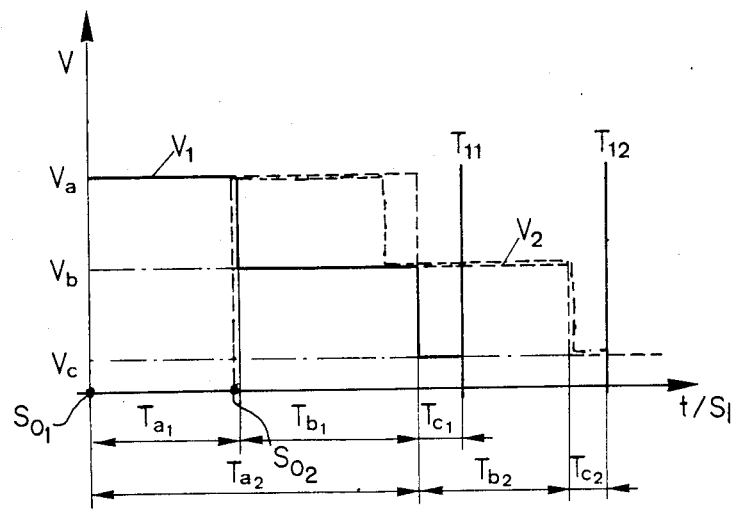
FIG. 6a shows in a speed-time diagram an example of the control of the advance of the drive jaw in accordance with two different advance-time intervals of the force-impacted jaw on the arrangement according to FIG. 6.

In FIG. 6a there are shown, for instance, two courses of the decoder multiplex unit output signal as a function of two different time values stored in the storage 71. If a time interval $T_{11}$ found upon the testing of a sample is stored in the storage 71 then the decoder multiplexer 73 controls the speed of advance in the case of the next sample in accordance with curve $V_1$. In an initial phase $T_{a1}$ the jaw 1 is advanced with high speed $x_1$ in accordance with the signal introduced $S(v_a)$, in a second phase $T_{b1}$ with lesser speed and during the last phase $T_{c1}$ up to contact with the sample 15 with very slow speed in order to minimize the impact momentum. Of course, this speed/time function can also be developed so as to decrease continuously with the desired characteristic. If in accordance with FIG. 6 in the case of the one sample a time interval $T_{12}$ until contacting the sample has been determined then the decoder multiplex circuit 73 controls the advance of the jaw 1, in the case of the next sample for instance in accordance with $V_2$, in the manner that corresponding to the longer time interval $T_{12}$ and thus the obviously longer displacement path having longer time intervals $T_{a2}$, $T_{b2}$ it is advanced with high speed $V_a$ and medium speed $v_b$ and again brakes down to the lower speed $v_c$ only shortly before contacting the sample 15.

For the first pass after the placing in operation of the device the storage 71 can be set as indicated with the input unit 77.

It is now self-evident that also, in general, a velocity profile according to the advance path S can be controlled and adaptively optimized. For this purpose, the position of the jaw 1 need not necessarily be detected. The adaptation can be effected, with fixed advance speed succession in time, in the manner that the return path of the jaw 1 is shifted and from the corresponding starting position of this jaw is controlled with the predetermined speed-time profile. In this way, an adjustment of the advance-speed/advance-path profile is obtained. The horizontal axis of FIG. 6a remains valid for the absolute jaw displacement path $S_1$ with starting point $S_{01}$. For the adaptation the entire $V_1$ profile can be shifted to the new jaw starting point $S_{02}$, as shown in dash-dot line.

After the sample has been broken, the force-impacted jaw 7 will then be driven back, corresponding to the position then assumed by it, with the force of the force-producing member 13 in accordance with FIG. 1 which, depending on the masses contemplated, can lead to large mechanical stresses. If one considers, for instance, the gravitational pendulum as preferred force-producing member, it is clear that after occurrence of the break it will swing back and can swing beyond the zero position and thereby drive the jaw 7 against the jaw 1 and that in general the entire testing apparatus can be subjected to large stresses.

Figure 2:
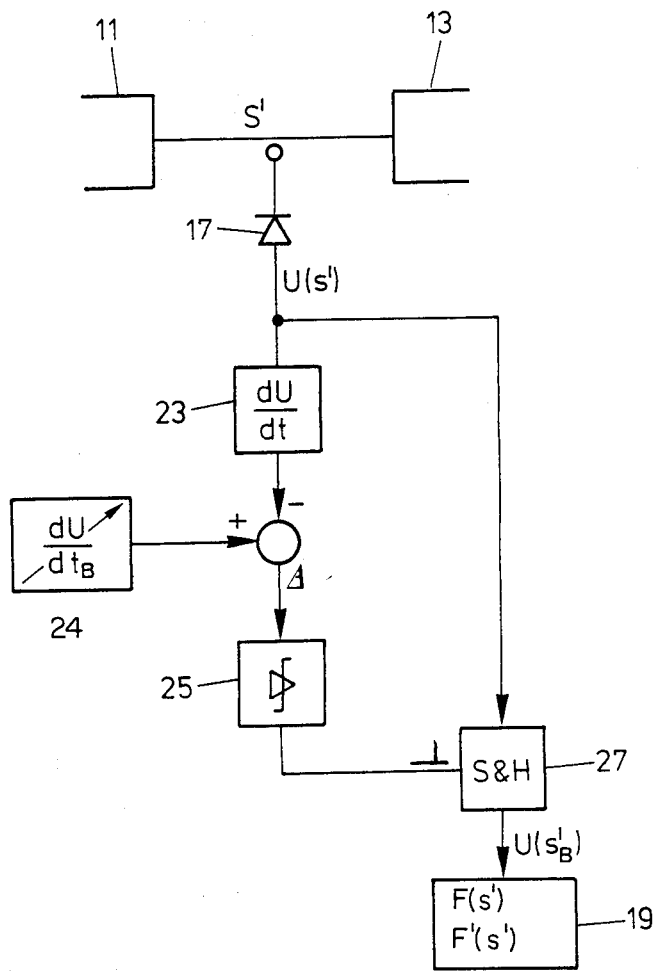
FIG. 2 is a functional block diagram concerning the detection of the time of breakage on the apparatus of FIG. 1.
Figure 7:
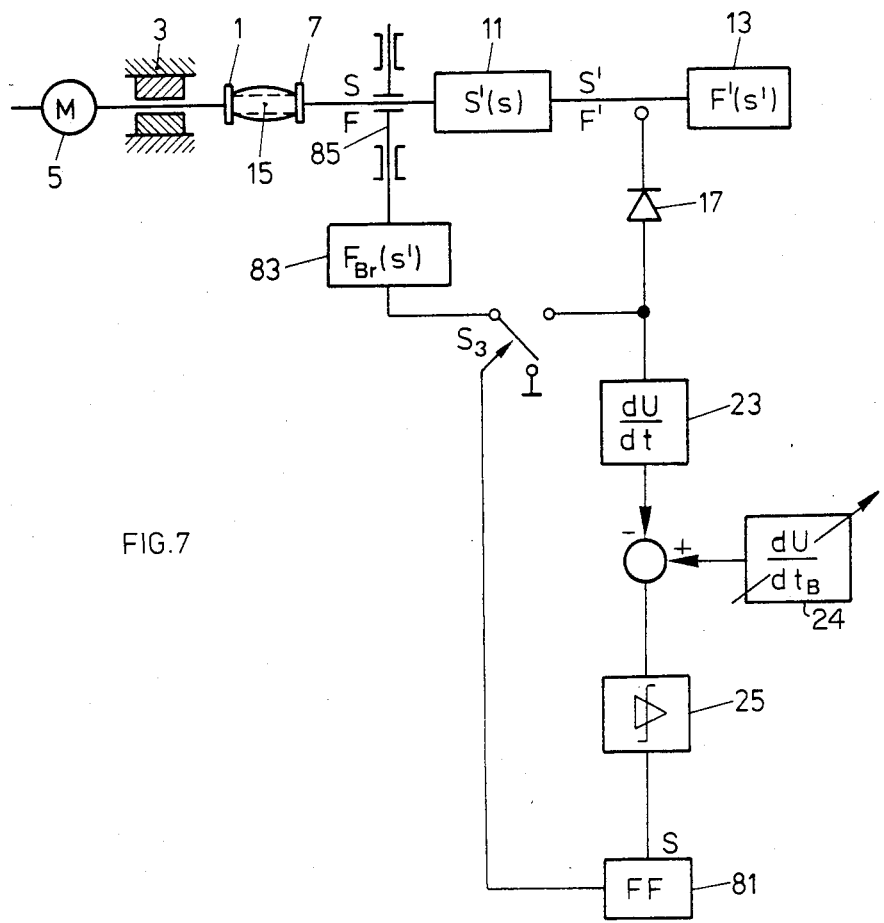
FIG. 7 is a block diagram of an apparatus according to the invention with the function blocks for controlled braking of the jaw-return movement.
Figure 9:
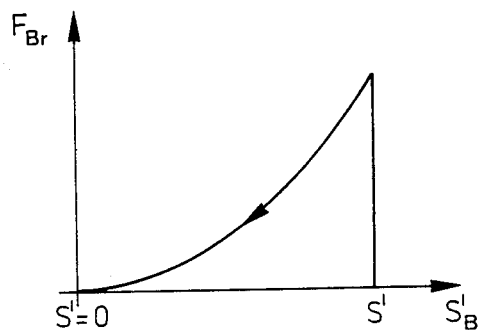
FIG. 9 shows, in a path/force diagram, the course of the braking force which can be obtained, for instance, with the arrangement of FIG. 8.

In order to prevent this, according to FIG. 7, in the manner already shown on basis of FIGS. 1 and 2, the path detector 17, the differentiation unit 23, and the subsequent comparator 25 by which the instantaneous time change of the displacement path of the jaw 7 is compared with the break-specific $dU/dt_B$ which can be introduced, are employed such that, upon the occurrence of the break a bistable element 81 is set and closes a connecting switch $S_3$ which connects the output of the path detector 17 to a brake control unit 83. The brake control unit 83 acts on the output side on a brake 85, shown diagrammatically in FIG. 7, which acts on the jaw 7 so that the brake brakes the jaw 7 as a function of the output signal of the path detector 17. The dependence of the braking force $F_{BR}$ on the displacement path S', detected by the detector 17, is shown, for example, in FIG. 9, from which it can be noted that at the time of the break, i.e. upon a displacement path $S'_B$, a high braking force is exerted on the jaw 7, which force is reduced continuously with decreasing displacement path with respect to the zero position of the jaw so that the jaw 7 is brought continuously, without overswing, into its zero position with $S'=0$.

Figure 8:
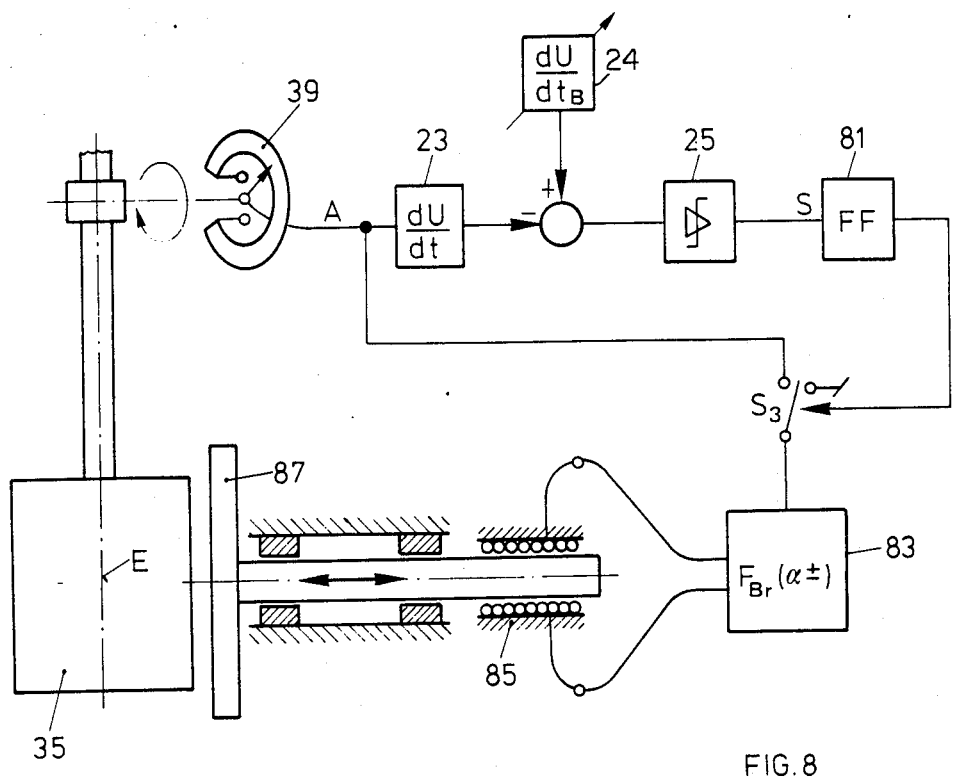
FIG. 8 is a more detailed block diagram of the apparatus according to FIG. 7 with gravitational pendulum.

In accordance with FIG. 8, this is so carried out in an apparatus in which, in accordance with FIG. 3, the force-producing member 13 of FIG. 1 is realized by a gravitational pendulum 35. The signal A tapped off from the potentiometer 39, sets via the differentiation unit 23, the comparator 25, upon detection of the break, a bistable element, such as a flip-flop 81, which then, similar to FIG. 7, closes the switch $S_3$. Via the brake control unit 83 to which the output signal A of the potentiometer 39 is then connected, a moving coil 85 is energized with pre-established dependence on the angle alpha, by which coil a brake plate 87 is first of all applied strongly against the pendulum 35 and then increasingly less strongly upon a decrease in the angle alpha, the plate 87 lying parallel to the plane E of the pendulum and being pressed perpendicular to said plane against the pendulum 35. In this way it is possible to bring even heavy pendulum masses rapidly, and nevertheless optimally damped, into the zero position.

It is self-evident that the braking device described with reference to FIGS. 7 and 8 and the corresponding method of braking can be realized advantageously in combination with the features of the apparatus which have been explained on basis of the preceding figures.

Instead of the path-dependent control via a path detection of brake members provided for the return movement of the loading jaw it is also entirely possible, and in certain cases simpler, to provide a brake member which, based on a fixed braking-force displacement path function, exerts a varible braking force on the loading jaw in accordance with a pre-established time function.

Figure 10:
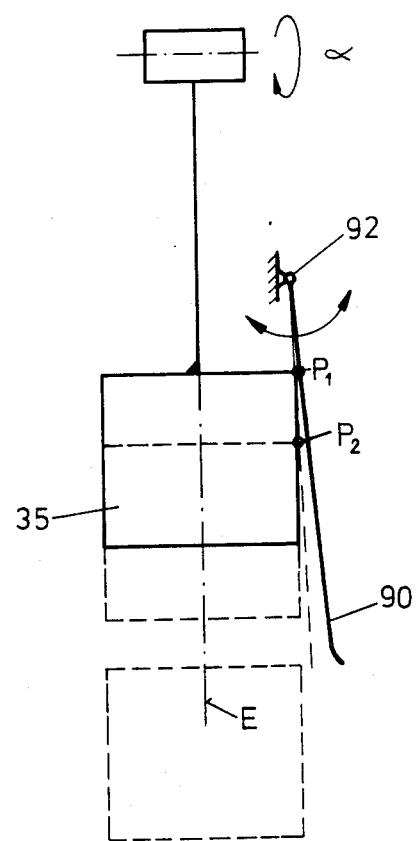
FIG. 10 is a diagrammatic showing of the path-variable braking of the jaw return movement.

Such an arrangement is shown in FIG. 10. The pendulum 35, shown by analogy to FIG. 8, coupled with the loading jaw 7, as already described above, operates together with a brake plate 90 which is mounted on an articulation 92 whose swivel axis lies parallel to the plane of swing E of the pendulum.

The pendulum 35 is shown in solid line in its deflected position. The plate 90 then lies in a region $P_1$ against the pendulum. Corresponding to the weight of the plate 90 and the lever arm between the point of application $P_1$ and the axis 92, the plate 90 then exerts a relatively strong braking pressure on the pendulum 35. The pendulum 35 slides slowly into the positions shown in dashed line, i.e. towards its position of rest. With decreasing deflection, the point of application of the plate 90 against the pendulum 35 also shifts, for instance to $P_2$, and the lever arm between this point of application, in this case $P_2$, and the axis 92 also becomes increasingly longer, so that the braking pressure exerted by the plate 90 becomes increasingly less until, when the pendulum 35 has reached its position of rest, plate 90 now only exerts a minimum pre-established force on the pendulum. Upon advance of the jaw, the brake is in general released, the plate 90 pushed away in accordance with FIG. 10.

We claim:

1. A method of testing the mechanical resistance of a sample of material comprising the steps of:
   (a) positioning said sample on a path of motion of two pressing jaws which are movable relative to each other, both towards and away from each other, when said jaws are apart from each other;
   (b) moving at least one of said two jaws so as to bring said two jaws relatively closer to each other and thereby bring both of said two jaws into contact with said sample;
   (c) automatically controlling the speed of said jaws relative to each other, from a high speed at the beginning of said moving, to a low speed just before both of said two jaws have made contact with said sample, to minimize the contact impact of said jaws and said sample and to simultaneously minimize the approach time of said jaws to said sample;
   (d) pressing said two jaws together with said sample therebetween; and
   (e) registering a pressing force and mechanical deformation of said sample.

2. The method of claim 1, wherein
said speed is controlled according to a preselected characteristic from said high speed to said low speed during movement of said two pressing jaws for testing a first sample;
said contacting of said two jaws and said sample is detected; and
said characteristic is automatically adjusted as a function of when said contacting has been detected for testing a second sample to further minimize the contact impact of said two jaws and said second sample and the approach time of said two jaws to said second sample by automatic learning from previous testing.

3. Apparatus for testing the mechanical resistance of a sample of material comprising:
   (a) two pressing jaws movable relative to each other, both toward each other from a separated position and away from each other into said separated position;
   (b) driving means operable for driving at least one of said two pressing jaws so as to change the separation of said two jaws relative to each other;
   (c) speed control means operable for controlling said driving means so as to drive said at least one jaw to change said separation at a high speed when said two jaws have just left said separated position relative to each other, and with a predetermined characteristic of speed versus displacement of said two jaws, from said high speed to a low speed after a predetermined displacement, to minimize the contact impact of said two jaws and a sample therebetween and to simultaneously minimize the approach time of said two jaws to said sample;
   (d) registering means for registering a pressing force between said two jaws and a mechanical deformation of said sample between said two jaws.

4. The apparatus according to claim 3, further comprising:
further registering means for registering initial data indicative of said relative motion of said two jaws toward each other, and of the contacting of said sample therebetween;
said speed control means comprising adjusting means to adjust said predetermined characteristic; and
said adjusting means being controlled in response to said initial data from said further registering means, to adjust said characteristic for a next sample to be tested.

5. A method of testing the mechanical resistance of a sample of brittle material comprising the steps of
   (a) positioning said sample on a path of motion of two movable pressing jaws; said path including respective starting positions of said two jaws;
   (b) driving at least one of said two jaws so as to bring both of said two jaws into contact with said sample;
   (c) further driving said one of said two jaws and thereby also driving said sample and the second of said two jaws;
   (d) providing a loading force opposing said drive on said second of said two jaws; said loading force progressively rising with the displacement of said second jaw being driven by said first jaw along said path of motion;
   (e) registering collapse of said sample between said two jaws and generating a collapse indicative signal; and
   (f) initiating a braking force on said second jaw after occurrence of said collapse indicative signal for opposing said loading force, so as to prevent said two jaws from hitting each other after collapse of said brittle material sample.

6. The method according to claim 5, including
returning said second jaw to its respective starting position; and
controlling said braking force in dependency upon said displacement of said second jaw in order to minimize return time of said second jaw to its respective starting position.

7. The method according to claim 6, wherein said respective starting position of said second jaw is the position of said second jaw prior to said displacement thereof by said first jaw.

8. The method according to claim 5, including registering said displacement of said second jaw; said braking force being controlled so as to diminish in dependency upon said displacement as said displacement diminishes after said collapse of said sample.

9. The method according to claim 8, including controlling said braking force by negative feedback control; a predetermined amount of said displacement being preselected as a controlling variable and said registered displacement being used as a controlled variable.

10. The method according to claim 5, including swinging a gravitational pendulum around an axis by an angle dependent upon said displacement, by action of said second jaw, and thereby providing said loading force; and providing said braking force as a frictional force acting at least substantially in the direction of said axis on said pendulum.

11. The method according to claim 8, wherein said frictional force is controlled to diminish as said displacement diminishes.

12. The method according to claim 5, wherein a time derivative of said displacement is registered and compared with a preselected time derivative for registering collapse of said sample and generating said collapse indicative signal.

13. An apparatus for testing the mechanical resistance of a brittle sample of material, comprising:

(a) a first pressing jaw and a second pressing jaw for retaining said brittle sample therebetween for said testing;

(b) driving means to drive said first pressing jaw in a first direction toward said second pressing jaw and thereby move said sample and said second pressing jaw in said second direction;

(c) force generating means for generating a force on said second pressing jaw in a direction which opposes said first direction; said generated force progressively rising with displacement of said second pressing jaw in said first direction;

(d) registering means for registering collapse of a sample interposed between said first and said second pressing jaws and generating a collapse indicative signal; and (e) braking means for acting with a brake force on said second pressing jaw and enabled by said collapse indicative signal to prevent said first and said second pressing jaws from hitting each other after collapse of said brittle sample.

14. The apparatus according to claim 13, said brake means generating a brake force on said second pressing jaw which, after said brake means being enabled, decreases with decrease of said displacement of said second jaw in said first direction.

15. The apparatus according to claim 14, further comprising registering means for registering said displacement of said second pressing jaw in said first direction; said registering means generating a signal dependent upon said displacement registered;

said brake means comprising control means to control said brake force; said control means being responsive to said signal dependent upon said displacement.

16. The apparatus according to claim 15, further comprising presetting means for presetting a predetermined value for said displacement; said predetermined value and said signal dependent upon said registered displacement being fed to a difference forming unit, which generates an output signal according to a difference of said predetermined value and said dependent signal; said output signal according to said difference being provided to said control means as a control deviation signal for a negative feedback control of said brake force according to said displacement.

17. The apparatus according to claim 13, said force generating means comprising a gravitational pendulum coupled to said second jaw and swingably mounted on an axle; said brake means comprising friction means acting on said pendulum with a friction force in a direction substantially parallel to said axle.

18. The apparatus according to claim 17, said friction means comprising a second gravitational pendulum, frictionally in contact with said first gravitational pendulum; the axle of said second gravitational pendulum being arranged substantially perpendicularly to said axle of said first gravitational pendulum.

19. The apparatus according to claim 13, comprising registering means for registering a displacement of said second pressing jaw in said first direction; said registering means generating a signal dependent upon said registered displacement;

preselecting means for preselecting a return speed of said driving means for said first pressing jaw and generating an output signal indicative of said return speed;

said signal dependent upon said displacement and said output signal from said preselecting means being fed to a dividing unit for generating a return time control signal;

said return time control signal being fed to an enabling input of said drive means to enable said drive means for returning said first pressing jaw for a length of time at least as great as a quotient of said displacement and said preselected return speed.

20. The apparatus according to claim 13, wherein said second jaw is linearly moveable;

said force generating means comprises a gravitational pendulum, coupled to said second jaw and swingably mounted on an axle; and further comprising angle registering means to register a swing angle of said pendulum as a function of a displacement of said second jaw;

said angle registering means generating an output signal according to said angle which is fed to an input of a sine function unit; said sine function unit generating an output signal proportional to the sine of said angle in response to said output signal of said angle registering means.

21. The apparatus of claim 20, said output signal of said angle registering means being fed to said sine function unit via an adjustable offsetting unit to correct said output signal of said angle registering means according to an angular difference between a true vertical direction of the apparatus and a direction of said pendulum at a time when said first pressing jaw first drivingly acts on said second pressing jaw.

22. The apparatus according to claim 21, said gravitational pendulum being coupled by a lever to said second jaw, one end of which lever is swingably mounted on said second jaw, the other end of which is swingably mounted on said pendulum; said output signal of said angle measuring means being further fed to a linearization unit, which generates at its output a correction signal as a function of said output signal of said angle registering means; said output signal of said sine function unit and said correction signal being multiplied by a multiplier unit, the output signal of which is substantially proportional to said displacement of said second jaw.

23. The apparatus according to claim 22, said gravitational pendulum comprising a two-armed pendulum lever, said two arms being firmly joined at respective ends of said arms and swingably mounted on said axle at these respective ends, said linearization unit generating an output signal H as said correction signal according to $$H(\alpha) = \frac{\cos\beta_1}{\cos(\beta_1 + \gamma - \alpha)}$$

and $$\beta_1 = \arcsin\left(\frac{l_4 - l_1\cos(\gamma - \alpha)}{l_2}\right);$$

wherein:
$H(\alpha)$: is the output signal of said linearization function;
$\alpha$: is said angle according to the output signal of said angle registering means;
$\gamma$: is the angle between said two arms of said pendulum;
$l_1$: is the length of one of said two pendulum arms swingably mounted on said lever and measured between said axle on which said pendulum is swingably mounted and said swinging mount on said lever;
$l_2$: is the length of said lever measured between said swingable mount to said second jaw and said swingable mount to said one arm of said pendulum;
$l_4$: is the shortest distance between said axle and a straight line defining the linear moving path of said second jaw; and
$\beta_1$: is the momentary angle between said lever and said straight line.

24. The apparatus according to claim 13, wherein said registering means for registering collapse of a sample comprises means for detecting the time derivative of the distance between said two jaws and for generating an output signal in dependency upon said time derivative; further comprising presetting means for generating a reference signal; said output signal of said time derivative means and said reference signal being fed to comparing means for generating an output signal when said registered time derivative exceeds a time derivative value derived from said reference signal.

25. A method of testing the mechanical burst load of a brittle sample of material comprising the steps of:
(a) positioning said sample between two jaws;
(b) squeezing said two jaws together with said sample therebetween with a rising squeezing force;
(c) registering a time derivative of a distance between said two jaws which is indicative of a time derivative of the extent of said sample between said two jaws;
(d) comparing said registered time derivative with a preselected value; and
(e) registering said squeezing force as soon as said registered time derivative exceeds said preselected value.

26. The method according to claim 25, wherein said time derivative of a distance between said two jaws is registered according to a time derivative of a displacement of at least one of said two jaws.

27. An apparatus for testing the mechanical burst load of a brittle sample of material, comprising:
(a) two pressing jaws;
(b) driving means operable to relatively move said two pressing jaws toward and away from each other;
(c) registering means operable to register a time derivative of a distance between said two jaws and generate an output signal as a function of said registered derivative;
(d) preselecting means to preselect a reference value signal;
(e) comparing means for comparing said output signals of said registering means and of said preselecting means, said comparing unit generating an output signal as soon as said output signal of said registering means exceeds said reference value signal; said output signal of said comparing unit being indicative of a collapse of said brittle material between said two pressing jaws; and
(f) further registering means to register a squeezing force between said two pressing jaws upon said collapse of said brittle material.

28. The apparatus according to claim 27, wherein said time derivative of a distance between said two jaws is registered as a function of a time derivative of a displacement of at least one of said jaws.

* * * * *